United States Patent [19]

Prue

[11] Patent Number: 5,142,707

[45] Date of Patent: Sep. 1, 1992

[54] ADDITIVE INJECTION UNIT FOR A MARINE TOILET SYSTEM

[76] Inventor: Frederick Prue, P.O. Box 229, Billerica, Mass. 01821

[21] Appl. No.: 518,538

[22] Filed: May 2, 1990

Related U.S. Application Data

[63] Continuation-in-part of Ser. No. 273,993, Nov. 1, 1988, abandoned, and a continuation-in-part of Ser. No. 419,543, Oct. 10, 1989, abandoned.

[51] Int. Cl.$^5$ ............................ A61L 2/16; E03D 9/02
[52] U.S. Cl. ......................................... 4/222; 222/522
[58] Field of Search ........................... 4/222, 225, 226; 222/514, 522, 523, 559

[56] References Cited

FOREIGN PATENT DOCUMENTS 501854 11/1954 Italy .......................................... 4/225

*Primary Examiner*—Charles E. Phillips
*Attorney, Agent, or Firm*—Allegretti & Witcoff, Ltd.

[57] ABSTRACT

A unit for injecting a disinfectant, deodorant or the like into the inlet stream of flushing water as it is pumped into the bowl of a tankless marine toilet. The injection unit is preferably constructed of commercially-available plastic plumbing components. The main body of the unit provides an additive reservoir which surrounds the flush water inlet pipe and is formed from a conventional plastic sanitary tee jointed fitted at each end with plastic size-reduction bushings. The two bushings connect the injection unit to the flush water inlet tubing and also support an interior flow pipe. Holes drilled at angles in the flow pipe divert a portion of the flush water through the additive reservoir where it mixes with and dissolves the additive (normally a water soluble disk of the type typically placed in the tank of a household toilet). A slidable elastic ring surrounding the interior flow pipe may be adjusted to vary the amount of diverted fluid and hence the amount of additive injected into the flush water stream. The unit further provides an access opening for introducing fresh water into the vessel's plumbing system for cleaning, and/or to introduce cleaning, lubricating or winterizing materials into the plumbing system to simplify maintenance. A flushing cap and hose may be attached to the injection unit to introduce a cleaning or winterizing solution to be pumped into the system from a supply container.

3 Claims, 5 Drawing Sheets

5,142,707

ADDITIVE INJECTION UNIT FOR A MARINE TOILET SYSTEM

CROSS REFERENCE TO RELATED APPLICATIONS

This application is a continuation-in-part of U.S. application Ser. No. 07/273,993 filed on Nov. 11, 1988 and U.S. patent application Ser. No. 07/419,543 filed on Oct. 10, 1989 both now abandoned.

BACKGROUND OF INVENTION

This invention relates generally to a device for introducing additives into a fluid flow and, more specifically, to a device for combining sanitizing, deodorizing, lubricating or winterizing additives with the flush-water flow into a tankless toilet of the type used in pleasure boats and travel trailers.

Conventional household toilets have a flush-water holding tank typically mounted above the toilet bowl. The holding tank is filled to a preset level with water so that, when the toilet is flushed, a substantial quantity of water is available to provide a thorough flushing action.

Marine toilets typically installed in pleasure craft have no tank. Instead, a flushing pump is used to propel flushing water though a water supply conduit which extends from an intake opening in the boat's hull. In this way, seawater rather than fresh water can be used to flush the toilet, reducing the size and weight of the toilet and avoiding unnecessary consumption of the on-board supply of fresh water.

Although the conventional "tankless" marine toilet performs its basic functions satisfactorily, it has significant shortcomings. Standing water in the toilet system often creates odors which are particularly unpleasant in the small and poorly ventilated confines of the craft's cabin space. The use of seawater for flushing, rather than fresh water, aggravates the problem because seawater typically contains salt, microorganisms, plant life, and other contaminants which often intensify the odors.

The flushing water used in household, tank-type toilets can be conveniently disinfected and deodorized using commercially available additives which can be placed in the toilet's tank. These additives typically take the form of disks of water-soluble compounds which dissolve slowly into the flushing water when submerged. Because these additives are designed for use in the household toilet's holding tank, which does not exist in a marine toilet unit, a need exists for an equally effective method of disinfecting, deodorizing and lubricating a marine toilet system.

It is accordingly a principal object of the present invention to disinfect and deodorize the flushing water supplied to a "tankless" toilet of the type typically used in marine plumbing systems.

It is a further and related object of the present invention to simplify the task of cleaning, lubricating and winterizing a marine plumbing system using one or more tankless toilets.

It is still another object of the present invention to disinfect, deodorize, clean, lubricate and/or winterize a toilet system by employing a device which is readily installable, easy to maintain, and which uses commercially available disks containing a composite of disinfectant, detergent and deodorant materials. These disks are manufactured for primarily for use with tank-type toilets and are widely available.

It is an additional object of the present invention to introduce a soluble additive into the flushing water of a toilet system by means of a device which may be constructed using mass-produced, readily available parts which, though manufactured for different purposes, may be advantageously combined to produce a low cost unit.

These and other objects, features and advantages of the present invention may be more clearly understood by considering the following detailed description of a preferred embodiment of the invention. In the course of this description, reference will frequently be made to the attached drawings.

DESCRIPTION OF THE PREFERRED EMBODIMENT

Figure 1:
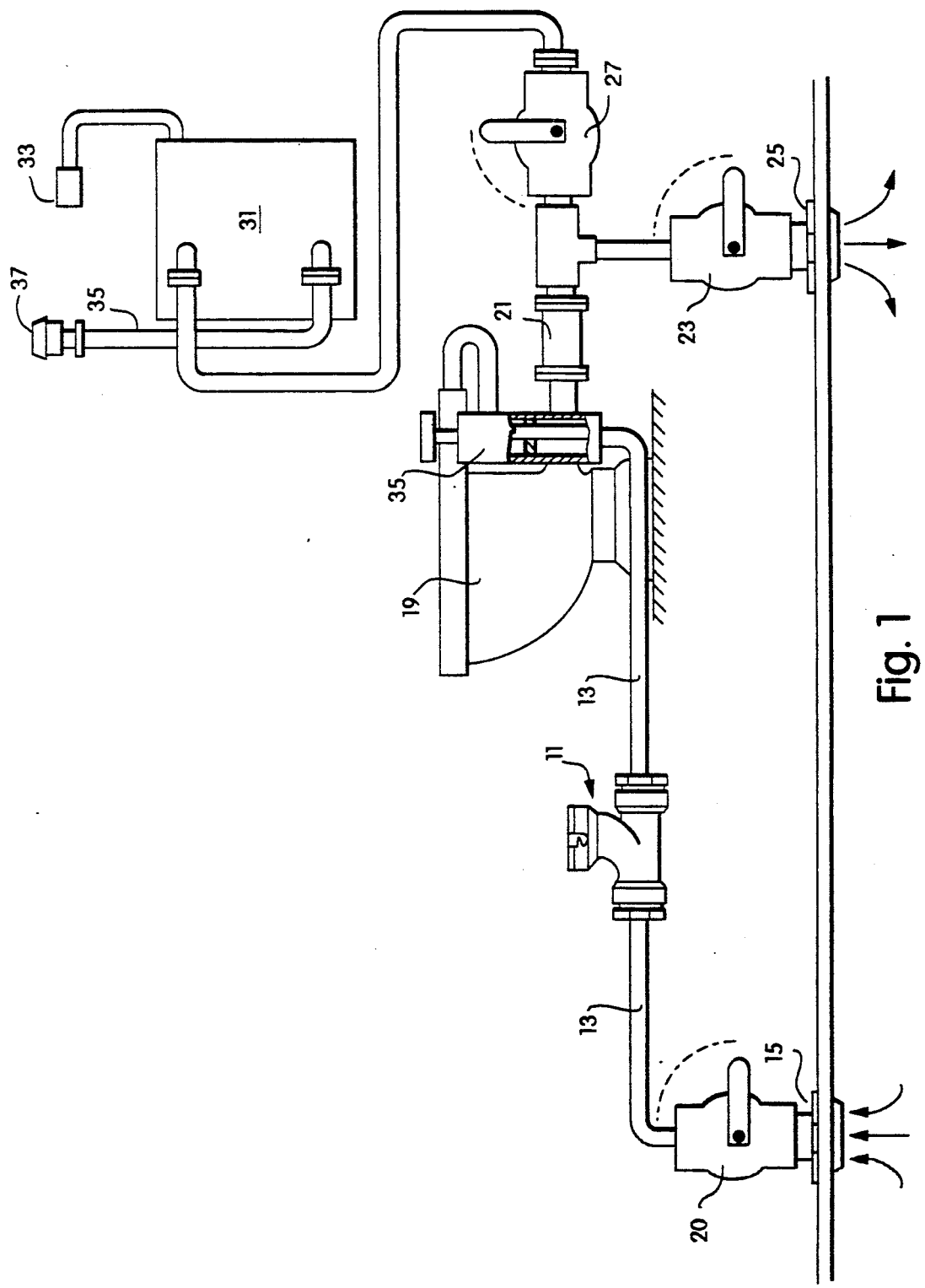
FIG. 1 depicts a marine toilet system which employs the principles of the present invention to sanitize, deodorize, lubricate, clean and/or winterize the flush water and the fluid carrying components of a marine plumbing system employing a tankless toilet.

The principles of the present invention may be applied to particular advantage to deodorize, lubricate and clean a tankless marine toilet system. These objectives are accomplished by means of an additive injection unit which is connected in the flush water intake as indicated generally at 11 in FIG. 1. The injection unit 11 is serially connected with a flush water conduit 13 which carries flushing water from a through-the-hull intake port 15 to a toilet bowl 19. A gate valve 20 connects the conduit 13 to the intake port 15. When closed, the valve 20 prevents sea water from entering the toilet system via the intake port 15.

Waste from the toilet bowl 19 flows through a drain conduit 21 and then passes either through a gate valve 23 to a through-the-hull outlet port 25, or alternatively through a gate valve 27 to a collection tank 31. When the waste is to be expelled through the outlet port 25, the gate valve 23 is open and the valve 27 is closed. When the waste is to be placed in the collection tank 31, valve 23 is closed and valve 27 is opened. Collection tank 31 is provided with a vent 33 and a waste removal conduit 35 which extends to a deck plate 37 which provides access to the collection tank for waste removal.

In order to provide an adequate flow of flushing water, a hand-operated flushing pump of the type illustrated at 35 in FIG. 1 may be serially connected with the flush water conduit 13 adjacent the toilet bowl 19. Other pumping mechanisms may be employed, both in the flush water intake and in the outlet drainage conduits, to provide the desired flows.

Figure 2:
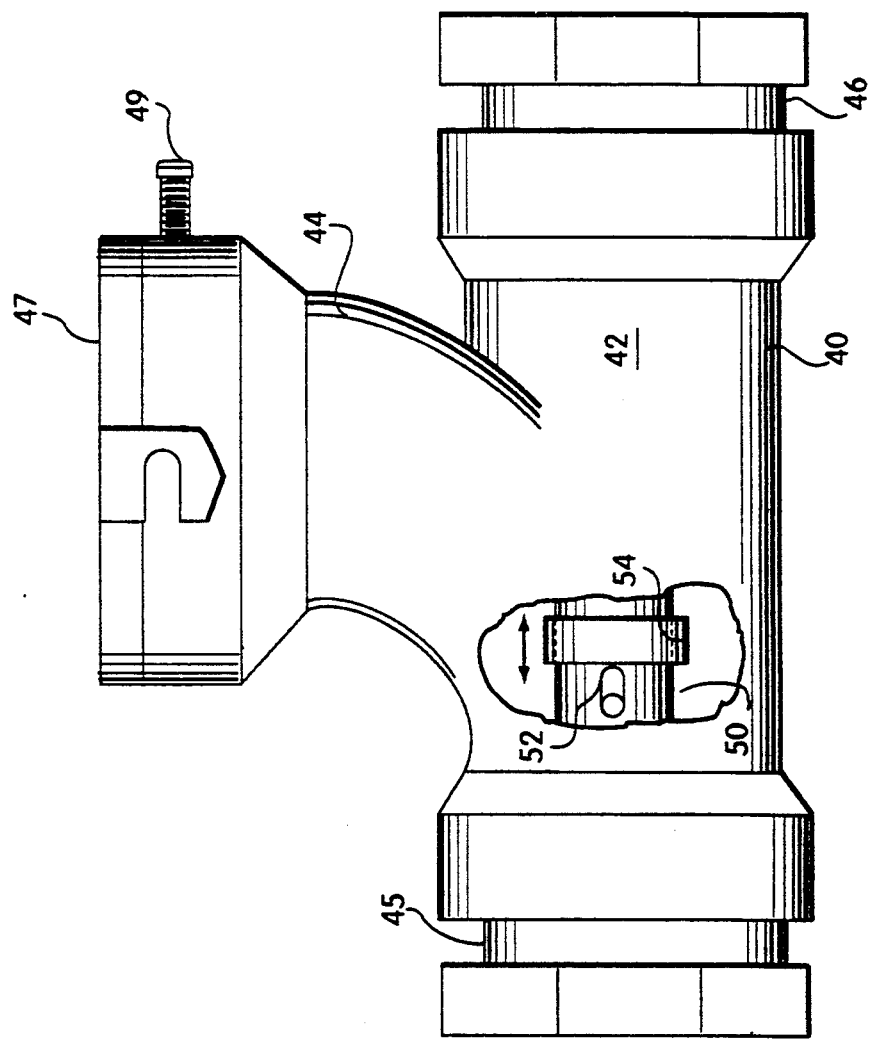
FIG. 2 is a side elevational view depicting the major elements of an additive injecting unit contemplated by the invention.

FIG. 2 of the drawings provides an enlarged view of the exterior of the additive injection unit 11. The main body of the unit 11 is formed by a conventional sanitary pipe tee joint 40 having a transverse pipe section 42 and an outwardly extending branch section 44. The opposing ends of the transverse section 42 terminate at mouth openings into which standard size-reduction bushings 45 and 46 are fitted. The mouth opening at the end of the branch section 44 is sealed with a twist-on sealing cap 47 secured against rotation by a set screw 49.

The sanitary tee joint 40, the bushings 45 and 46, and the cap 47 together form a cavity which surrounds an interior flow pipe 50 (seen in FIG. 2 through the cutaway section of the tee joint 40). As will be discussed in more detail later, one or more fluid passageways, one of which is seen at 52 in FIG. 2, are drilled at an angle through the interior flow pipe 50 to permit a portion of the flush water flow in pipe 50 to enter the surrounding additive reservoir cavity. Downstream from the inlet hole 52, one or more outlet passageways 53 (seen in FIG. 3) return the diverted portion of the flow to the interior of flow pipe 50.

An additive, typically a disk of a commercially available water-soluble disinfectant/detergent/deodorant (of the type normally placed in the tank of household toilets), is inserted into the mouth of the branch section 44 by removing the cap 47, and then resealing the cap 47 after the additive is in place.

An annular elastic ring seen at 54 in FIG. 2 surrounds the interior pipe 50, maintaining a slidable friction fit with the pipe 50. The ring 54 may be moved axially along the length of the pipe 50 in order to restrict, to varying degrees, the flow through the passageway(s) 52.

The tee joint 40 preferably takes the form of a Genova 2"×2"×2" sanitary pipe tee joint which presents three, 2-inch inside diameter mouth openings. This standard plumbing component is readily available and provides significant advantages when used to implement the present invention. Formed from plastic, the tee joint and the parts with which it mates are naturally resistant to the corrosive effects of seawater. The cylindrical shape of the transverse pipe section 42, in combination with the outwardly extending branch section 44, combine to form an additive reservoir cavity which promotes the desired flow of a diverted portion of the flush-water as well as adequate interior space to receive and retain the additive, while conforming to the flush water inlet conduit 13 to meet the confined spatial requirements of a marine toilet system. The ends of the transverse pipe section 42 of the tee joint 40 are suitably closed by the mating Genova 2"×¾" plastic bushings 45 and 46, both of which are also standard components sized to mate with the mouth openings presented by the tee joint 40. The bushings 45 and 46 are secured in place by conventional PVC cement.

The interior flow pipe 50 is axially aligned with the transverse pipe section 42 of the tee joint 40 and is supported at each end by the bushings 45 and 46. The flow pipe 50 is formed from a 5¾" long section of ¾" outside diameter Genova CPVC plastic tubing.

Figure 3:
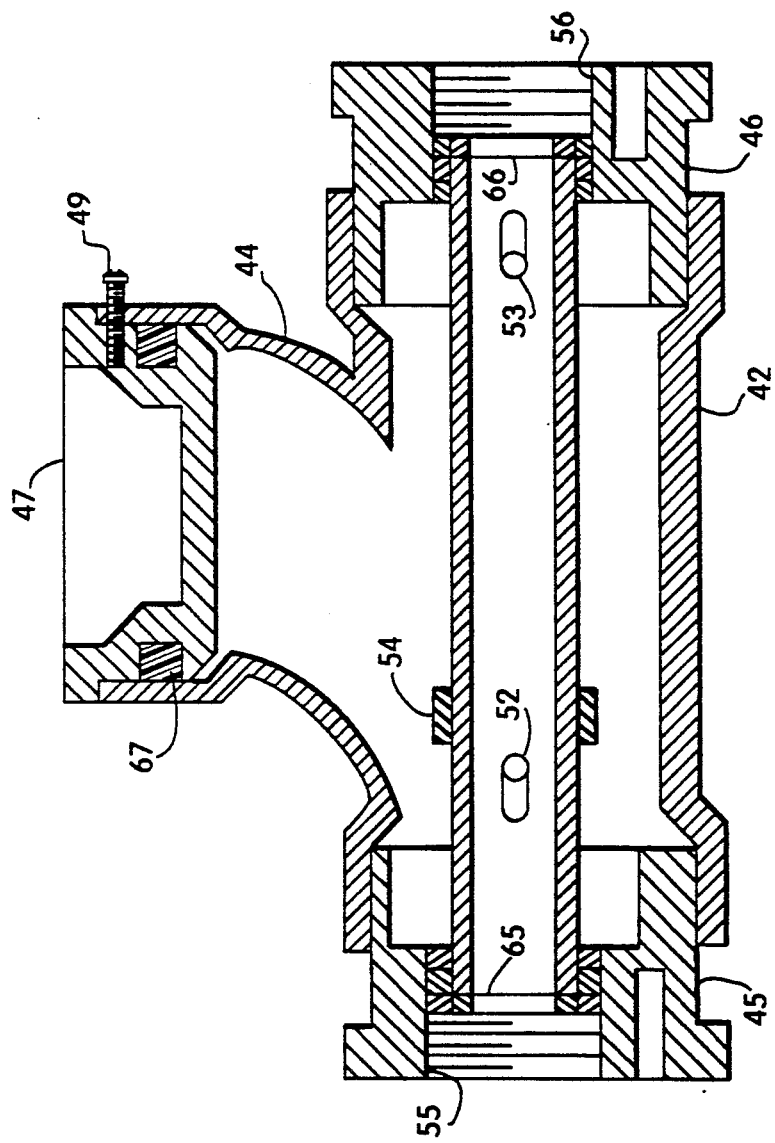
FIG. 3 is a side cross sectional view, taken along the line A—A seen in FIG. 4, of the additive injecting unit.

FIG. 3 provides a side cross sectional view of the additive injection unit 11 showing its construction in more detail. As seen in FIG. 3, the bushings 45 and 46 have interior threaded bores 55 and 56 respectively which receive ¾" male-threaded barbed hose fittings (not shown) which are used to connect the injection unit 11 to the flush water inlet conduit 13 as illustrated in FIG. 1.

The interior flow pipe 50, having a smaller outside diameter than the inside diameter of the bores 55 or 56, may be inserted through either bore and secured in place (about ¼ inch from the inner edge of each of the bushings 45 and 46) by means of hose washers seen at 65 and 66.

One or more inlet holes 52 are drilled at an angle through the upstream end of the flow pipe 50. These inlet holes are drilled at about a 45 degree angle to encourage the diversion of a portion of the flush water flowing through the interior flow pipe 50 into the additive reservoir cavity formed by the tee joint 40. The axial position of the slidable elastic ring 54 may be adjusted to partially or completely restrict the inlet aperture formed by the hole(s) 52, thereby allowing the cross-sectional area of the fluid flow path for the diverted flushing water to be variably restricted. In this way, the proportion of flush water that is diverted through the additive reservoir cavity may be controlled. The annular ring 54 may be easily removed and replaced in the unit 11 for periodic cleaning or adjustment by removing one of the washers 65 or 66 and pulling the flow pipe 50 half-way out of the tee joint, allowing the ring 54 to be reached for adjustment, removal or replacement through the mouth of branch section 44 (with cap 47 removed).

As seen in FIG. 3, the detachable cap 47 which covers the mouth of the branch section 44 of the tee joint 40 includes an annular recess which receives and retains an O-ring gasket 67. The gasket 67 provides a water-tight seal between the cap 47 and the mouth of branch section 44.

Figure 4:
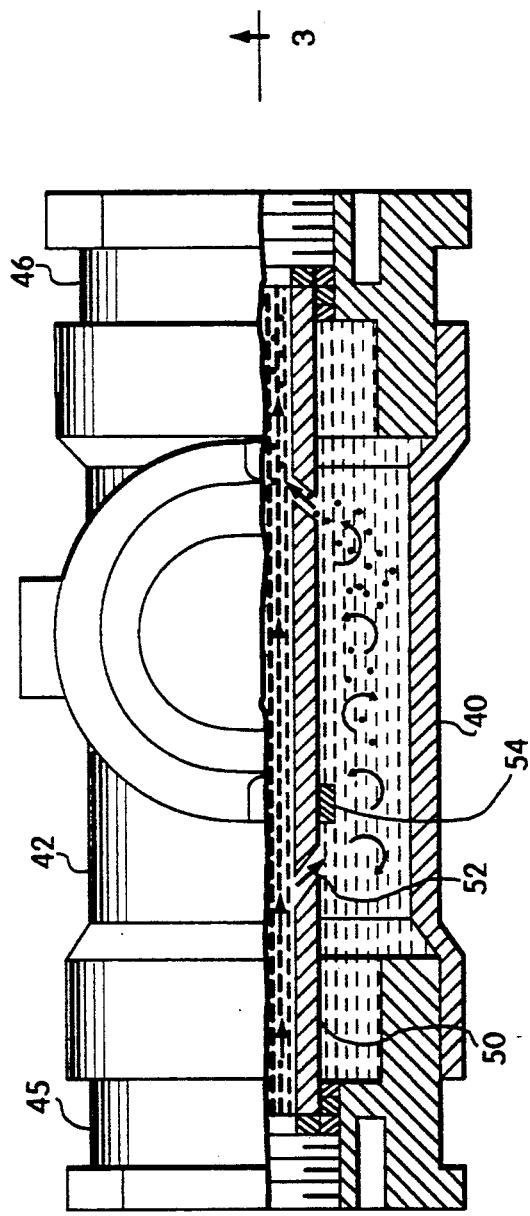
FIG. 4 is a top, partial cross-sectional view of the unit illustrating the manner in which a portion of the flush water flow is diverted within the unit to dissolve and collect an additive ingredient which is then injected into the main flushing water stream.

FIG. 4 is a top, partial cross-sectional view of the additive injection unit which more clearly depicts the manner in which additives are dissolved into and combined with that portion of the fluid flow which is diverted through the additive reservoir cavity. As seen in FIG. 4, seawater flows through the flow pipe 50 until it reaches the inlet hole 52 which is angled to induce a portion of the seawater to flow from the interior of the flow pipe 50 into and through the additive reservoir surrounded by the tee joint 40. In the reservoir, the diverted seawater is brought into turbulent contact with the additive material, dissolving a small portion of the additive, and returning through the downstream passageway formed by the outlet hole(s) 53 seen in FIG. 3. As noted earlier, the axial position of the slidable elastic ring 54 may be adjusted to control the amount of flush water diverted through the additive reservoir 22. This adjustability accommodates different flow pressures exhibited by different plumbing systems, and allows the amount of additive injected to be reduced to the minimum needed to achieve the results desired, thus conserving the additive so that it may be replenished less frequently.

In addition to deodorizing, lubricating and sanitizing the toilet system by introducing a measured quantity of additive into the normal flushing water inlet stream as heretofore described, the invention also permits the toilet system to be conveniently cleaned and/or winterized on a periodic basis. In normal operation of the system as shown in FIG. 1, seawater is drawn by the flushing pump 35 through the intake port 15 through the hull. In this case, the dissolved additive from additive injection unit 11 advantageously flows not only through the toilet bowl but through the toilet's drainage system, thereby sanitizing, deodorizing and/or cleansing the toilet bowl 19, the drainage conduits, and the contents of the collecting tank 31.

When it is instead desired to clean or winterize the toilet system, the gate valve 20 may be closed and pump 35 operated to purge the system of seawater. The detachable cap 47 may then be removed from the injecting unit 11 and fresh water added to the toilet system's flush-water inlet conduit 13 via the branch section 44. The pump 35 is then operated to pump the newly added fresh water through the system, thereby cleansing the system of accumulated salt and debris. If desired, a suitable detergent or other cleaning agent may be premixed with the fresh water before it is introduced into the plumbing system via the injection unit 11. In the same way, a winterizing or lubricating solution can then be added to the marine toilet system, typically when the vessel is placed in winter storage, providing a convenient and effective method of protecting the vessel's plumbing system against rust, corrosion, drying and/or frost damage.

Figure 5:
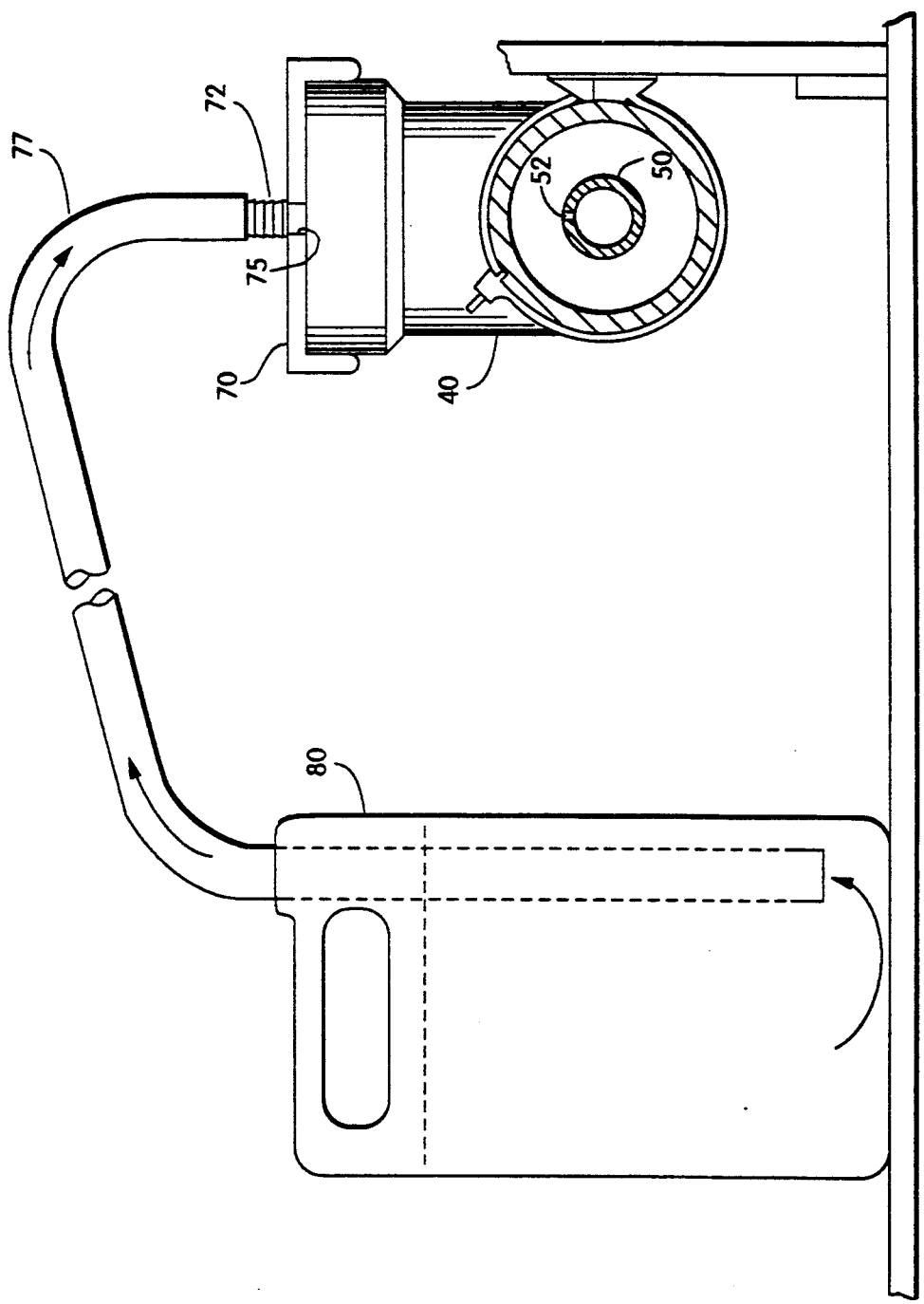
FIG. 5 is an elevational view showing the use of a special flushing cap and tubing used to conveniently introduce a cleaning or winterizing solution into the toilet system.

The removable cap 47 need not be closed while the cleaning or winterizing solution is being pumped into the system. The user may leave the cap 47 off and simply pour the solution into the additive reservoir through the mouth of the branch 44, replenishing the reservoir as needed as the solution is being pumped. For even greater convenience, the normal cap 47 may be replaced with a flushing cap 70 seen in FIG. 5 of the drawings.

The flushing cap 70 is provided with a cyclindrical hose fitting nipple 72 permanently affixed to the cap 70. A flexible feed hose 77 attached to the nipple 72 feeds fluid from a supply container 80 through a hole 75 in the cap 70. When the gate valve 20 (seen in FIG. 1) is closed, pumping creates a vacuum within the injection unit to draw solution from the supply container 80 through the flexible tubing 77 into the additive reservoir formed by the tee joint. The solution from container 80 then flows through both the passageways 52 and 53 into the flow pipe 50 and into the plumbing system. The direction of fluid flow through the passageway 52, which in normal operation conducts fluid from the pipe 50 into the additive reservoir as flushing water is being drawn through the open gate valve, reverses such that both the passageway 52 and the passageway 53 both conduct fluid from the reservoir into the pipe 50.

After the pumping system has been operated to flush fluid from the supply container 80 into the system, the flush cap 70 is removed, an new additive disk is placed in the additive reservoir, and the permanent cap 47 is again secured over the mouth of the branch section 44 by means of the set screw 49 seen in FIG. 3 to insure a pressure tight seal so that flushing water will be drawn through the gate valve 20 during normal flushing operation.

It is to be understood that the embodiment of the invention which has been described is merely illustrative of one application of the principles of the invention. Numerous modifications may be made by those skilled in the art without departing from the true spirit and scope of the invention.

What is claimed is:

1. An arrangement for introducing an additive into a fluid flow which comprises, in combination,
    a flow pipe formed from corrosion resistant plastic having a uniform diameter,
    means for connecting said flow pipe in series fluid-flow with a conduit, said means for connecting said flow pipe being formed from corrosion resistant plastic,
    a closed additive reservoir cavity formed by a main body section of said arrangement surrounding said flow pipe, said means for connecting said flow pipe in series flow relation, and a twist-on sealing cap covering an access passageway, said additive reservoir cavity comprising, in combination, a sanitary pipe tee joint having first and second circular mouths at opposing ends of a cylindrical transverse body pipe section and a third circular mouth at the outer end of a branch pipe section which extends radially outward from the middle of said transverse body pipe section, first and second annular size-reduction bushings inserted in and affixed to the said first and second mouths respectively for removably securing opposing ends of said flow pipe in a position extending axially through said transverse body pipe section,
    at least one inlet aperture and at least one return aperture through said flow pipe, both of said apertures providing a fluid flow path between the interior of said pipe and said additive reservoir cavity, and said inlet aperture being positioned upstream from said return aperture to induce a portion of the fluid flowing through said conduit to flow through said additive reservoir cavity,
    said access passageway leading into said additive reservoir cavity and being normally covered by said removable twist-on sealing cap which may be opened to permit an additive material to be introduced into said additive reservoir cavity and thereafter closed to provide a pressure tight seal for said additive reservoir cavity and to retain said material within said additive reservoir cavity, and
    adjustable means for variably restricting the fluid flow path through said inlet aperture, said additive reservoir cavity, and said return aperture whereby the volume of fluid diverted through said additive reservoir cavity may be adjusted to vary the amount of additive introduced into said conduit.

2. In a marine toilet system of the class comprising, in combination, a through-the-hull inlet for seawater intake, an entrance gate valve for regulating said seawater intake, a flushing water supply hose for channelling said seawater intake, a toilet bowl, and a pump for advancing flushing water through said hose to said bowl, an drain outlet in said boat hull for releasing waste, a gate valve for allowing passage of said waste through said drain outlet, a drain conduit for channelling waste from said toilet bowl to said from said gate valve, a holding tank for receiving and storing said waste and seawater intake, wherein the improvement comprises:
    an arrangement for introducing a fluid into the flush-water inlet conduit of a tankless toilet which comprises, in combination,
    a flow pipe formed from corrosion resistant plastic,
    a closed additive reservoir surrounding said flow pipe comprising a sanitary pipe tee joint formed from corrosion resistant plastic and having first and second circular mouths at opposing ends of a cylindrical transverse body pipe section and a third circular mouth at the outer end of a perpendicular body pipe section which extends radically outward from the middle of said transverse body pipe section, first and second annular bushings formed from corrosion resistant plastic and inserted in and affixed to the said first and second mouths respectively for removably securing opposing ends of said flow pipe in a position extending axially through said transverse pipe section, at least one inlet aperture and at least one return aperture through said flow pipe, both of said apertures providing a fluid flow path between the interior of said pipe and said additive reservoir, and said inlet aperture being positioned upstream from said return aperture to induce a portion of the fluid flowing through said inlet conduit to flow through said additive reservoir, adjustable means for variably restricting the fluid flow path through said inlet aperture, said reservoir and said return aperture comprising an annular bushing encircling said flow pipe and movable along the length of said flow pipe whereby the cross-sectional area of said inlet or return aperture may be varied, thereby variably restricting the fluid flow path.

3. An arrangement for sanitizing, deodorizing, cleansing, lubricating and/or winterizing "tankless" toilet systems of the type used in a boat comprising, in combination:

an inlet through the hull of said boat, an entrance gate valve for regulating the flow of water through said inlet, a tankless toilet mounted within said boat, a flushing water supply hose for channelling water from said entrance gate valve to said toilet, and an additive injection unit for introducing a fluid into said supply hose comprising, in combination, a flow pipe formed from corrosion resistant plastic, a closed additive reservoir surrounding said flow pipe, the outer wall of said reservoir being defined by a plastic sanitary pipe tee joint forming first and second circular mouths at opposing ends of a cylindrical transverse body pipe section of said joint, and a third circular mouth at the outer end of a branch pipe section which extends radically outward from the middle of said transverse body pipe section, and the end walls of said reservoir being defined by first and second annular plastic bushings in and affixed to the said first and second mouths respectively, said bushings further securing opposing ends of said flow pipe in a position extending axially through said transverse pipe section of said tee joint, at least one inlet aperture and at least one return aperture through said flow pipe, both of said apertures providing a fluid flow path between the interior of said pipe and said additive reservoir, and said inlet aperture being positioned upstream from said return aperture to induce a portion of the fluid flowing through said inlet conduit to flow through said additive reservoir, adjustable means for variably restricting the fluid flow path through said inlet aperture comprising an elastic ring encircling said flow pipe and movable along the length of said flow pipe whereby the cross-sectional area of said inlet aperture may be varied to adjustably restrict said fluid flow path.

* * * * *